(12) United States Patent
Eiler (10) Patent No.: US 9,594,879 B2
(45) Date of Patent: Mar. 14, 2017

(54) SYSTEM AND METHOD FOR DETERMINING THE ISOTOPIC ANATOMY OF ORGANIC AND VOLATILE MOLECULES

(71) Applicant: California Institute of Technology, Pasadena, CA (US)

(72) Inventor: John M. Eiler, Pasadena, CA (US)

(73) Assignee: California Instutute of Technology, Pasadena, CA (US)

( * ) Notice: Subject to any disclaimer, the term of this patent is extended or adjusted under 35 U.S.C. 154(b) by 532 days.

(21) Appl. No.: 13/656,577

(22) Filed: Oct. 19, 2012

(65) Prior Publication Data

US 2013/0124108 A1    May 16, 2013

Related U.S. Application Data

(60) Provisional application No. 61/550,272, filed on Oct. 21, 2011, provisional application No. 61/652,095, filed on May 25, 2012.

(51) Int. Cl.
*G06F 19/00* (2011.01)

(52) U.S. Cl.
CPC .................................. *G06F 19/703* (2013.01)

(58) Field of Classification Search
USPC .......................................................... 702/27
See application file for complete search history.

(56) References Cited

U.S. PATENT DOCUMENTS

| | | | |
|---|---|---|---|
| 3,849,656 A | 11/1974 | Wallington | |
| 5,194,732 A | 3/1993 | Bateman | |
| 5,347,125 A | 9/1994 | Holmes et al. | |
| 5,723,862 A | 3/1998 | Forman | |
| 6,297,501 B1 * | 10/2001 | Merren | 250/296 |
| 7,351,316 B2 | 4/2008 | Yoshida et al. | |
| 7,653,494 B2 | 1/2010 | Neacsu et al. | |
| 7,979,258 B2 | 7/2011 | Goldberg et al. | |

(Continued)

FOREIGN PATENT DOCUMENTS

| | | |
|---|---|---|
| EP | 1339 089 A1 | 8/2003 |
| EP | 2128791 A2 | 12/2009 |

(Continued)

OTHER PUBLICATIONS

Michael A. Baldwin, Protein Identification by Mass Spectrometry, Molecular & Cellular Proteomics 3.1, © 2004 by the American Society for Biochemistry and Molecular Biology, Inc. p. 1-9.*

(Continued)

*Primary Examiner* — Tung Lau (74) *Attorney, Agent, or Firm* — Lewis Roca Rothgerber Christie LLP (57) ABSTRACT

A computer implemented system and method for determining the isotopic anatomy of molecules. The system receives a user identified molecule that is to be analyzed, makes an initial guess as to the isotopic anatomy of the molecule, and iteratively refines the initial guess based on one or more observations made by the user. When sufficient iterations have been performed, the system outputs information about the isotopic anatomy of the molecule. The information may then be stored, displayed on a monitor, analyzed for making other conclusions, and/or printed.

38 Claims, 7 Drawing Sheets

(56) References Cited

U.S. PATENT DOCUMENTS

| | | |
|---|---|---|
| 8,895,915 B2 | 11/2014 | Schwieters et al. |
| 2002/0102610 A1 | 8/2002 | Townsend et al. |
| 2004/0046116 A1* | 3/2004 | Schroeder et al. ........... 250/281 |
| 2004/0083063 A1 | 4/2004 | McClure |
| 2005/0086017 A1 | 4/2005 | Wang |
| 2005/0255606 A1 | 11/2005 | Ahmed et al. |
| 2006/0228301 A1 | 10/2006 | Boros |
| 2007/0034810 A1 | 2/2007 | Hoyes |
| 2010/0108879 A1 | 5/2010 | Bateman et al. |
| 2011/0100222 A1 | 5/2011 | Reilly |
| 2013/0103337 A1* | 4/2013 | Eiler ............................... 702/86 |
| 2014/0097338 A1* | 4/2014 | Eiler ............................. 250/282 |

FOREIGN PATENT DOCUMENTS

| | | |
|---|---|---|
| WO | WO 94/07257 | 3/1994 |
| WO | WO 2011-128702 A1 | 10/2011 |
| WO | WO 2013/070304 A1 | 5/2013 |

OTHER PUBLICATIONS

Krishnan K. Palaniappan, Isotopic Signature Transfer and Mass Pattern Prediction (IsoStamp): University of California, Berkeley, California 94720, United States, Published: May 23, 2011, ACS Chem. Biol. 2011, 6, 829-836, p. 829-836.*
International Search Report and Written Opinion issued in PCT/US2012/061192, dated Mar. 28, 2012, 11 pages.
International Search Report and Written Opinion for PCT/US2012/061191, dated Mar. 29, 2013, 8 pages.
International Search Report and Written Opinion for PCT/US2013/064409, dated Jan. 16, 2014, 9 pages.
Mass Spectrometry: Quadrupole Mass Filter, Advanced Lab, Jan. 2008, 8 pages.
Rubakhin, Stanislav S., et al., A mass spectrometry primer for mass spectrometry imaging, National Institutes of Health, Public Access Author Manuscript, Apr. 7, 2011, 29 pages.
Van Galen, Peter M., Mass Spectrometry @ the Organic Chemistry Department, Nijmegen University, Sep. 2005, 47 pages.

* cited by examiner

SYSTEM AND METHOD FOR DETERMINING THE ISOTOPIC ANATOMY OF ORGANIC AND VOLATILE MOLECULES

CROSS-REFERENCE TO RELATED APPLICATIONS

This application claims the benefit of U.S. Provisional Application Ser. No. 61/550,272, filed on Oct. 21, 2011, entitled HIGH-RESOLUTION MASS SPECTROMETER AND METHODS FOR DETERMINING THE ISOTOPIC ANATOMY OF ORGANIC AND VOLATILE COMPOUNDS, and U.S. Provisional Application Ser. No. 61/652,095, filed on May 25, 2012, entitled SYSTEND METHOD FOR DETERMINING THE ISOTOPIC ANATOMY OF ORGANIC AND VOLATILE MOLECULES, the entire contents of each of which are incorporated herein by reference.

This application is also related to U.S. application Ser. No. 13/656,447, filed Oct. 19, 2012, the content of which is incorporated herein by reference.

STATEMENT REGARDING FEDERALLY SPONSORED RESEARCH OR DEVELOPMENT

This invention was made with government support under Grant No. EAR0949336 awarded by the National Science Foundation. The government has certain rights in the invention.

BACKGROUND

It is desirable to determine the isotopic composition, including position-specific and multiple substitutions, of a particular molecule in a user friendly manner which can be applied to different kinds of compounds. Because of the great number of unique isotopic versions of many molecules, any efficient method of analysis should generally be capable of observing the largest fraction of those species that is practical (in light of constraints imposed by time and/or sample size) and interpreting measurements of a sub-set of all possible isotopic species. In particular, it is desirable to balance the need for highly precise measurements of relative abundances of isotopic versions of a molecule—a generally time consuming analysis—against the desire to observe a large number of isotopic versions of each molecular species. Ideally, a measurement algorithm would enable both high precision analyses of a few species, poorer precision analyses of a large number of species, and a model which relates these data types to each other in a self-consistent fashion.

SUMMARY

Embodiments of the present invention are directed to a non-transitory computer readable medium embodying program instructions for execution by a data processing apparatus. The program instructions adapt the data processing apparatus for predicting an isotopic anatomy of a molecule. The program instructions include receiving information of a molecule having a plurality of isotopic species; generating a prediction of the isotopic anatomy of the molecule; invoking a mass spectrometer for making an observation; automatically refining the prediction of the isotopic anatomy of the molecule based on the observation; and generating an output indicative of the isotopic anatomy of the molecule.

According to one embodiment of the invention, the isotopic anatomy of the molecule is a mass spectrum of the molecule or the isotopic composition of the molecule.

According to one embodiment of the invention, the prediction of the isotopic anatomy considers presence of interferences and/or a fragmentation spectrum.

According to one embodiment of the invention, the prediction is based on the isotopic anatomy of a standard for the molecule having a known or assumed composition.

According to one embodiment of the invention, generating the prediction includes estimating abundance of one or more of the plurality of isotopic species via one or more algebraic operators that define relationships among the isotopic species.

According to one embodiment of the invention, the generating the prediction includes generating a predicted mass spectrum for the molecule.

According to one embodiment of the invention, making the observation includes performing a mass scan of one or more of the isotopic species and outputting a measured mass spectrum of the one or more isotopic species.

According to one embodiment of the invention, refining the prediction includes calculating a best fit between the measured mass spectrum and the predicted mass spectrum.

According to one embodiment of the invention, the refining the prediction includes identifying one or more of the plurality of isotopic species affected by the observation. The species affected by the observation may include species not expressly observed by performing the mass scan. According to one embodiment of the invention, the refining includes estimating abundances of the species not expressly observed, based on one or more algebraic equations that define relationships of the species not expressly observed, with species that are observed.

According to one embodiment of the invention, the observation is a measurement of relative abundance of two of the isotopic species.

According to one embodiment of the invention, refining the prediction includes refining relative abundance of two other isotopic species which relative abundance is not expressly measured.

According to one embodiment of the invention, the program instructions include recommending one or more of the plurality of isotopic species for observation. The recommendation may be based on estimated shrinking of a composition space based on observation of the recommended one or more of the plurality of isotopic species.

According to one embodiment of the invention, the program instructions include identifying a property of the molecule based on the predicted isotopic anatomy of the molecule; and outputting a recommendation based on the identified property. The identified property may be temperature.

BRIEF DESCRIPTION OF THE DRAWINGS

These and other features and advantages of the present invention will be better understood by reference to the following detailed description when considered in conjunction with the accompanying drawings, briefly described below.

DETAILED DESCRIPTION

In general terms, embodiments of the present invention are directed to a computer implemented system and method for determining the isotopic anatomy of molecules. The system receives a user identified molecule that is to be analyzed, makes an initial guess as to the isotopic anatomy of the molecule, and iteratively refines the initial guess based on one or more observations made by the user. When sufficient iterations have been performed, the system outputs information about the isotopic anatomy of the molecule. The information may then be stored, displayed on a monitor, analyzed for making other conclusions, and/or printed.

Figure 1:
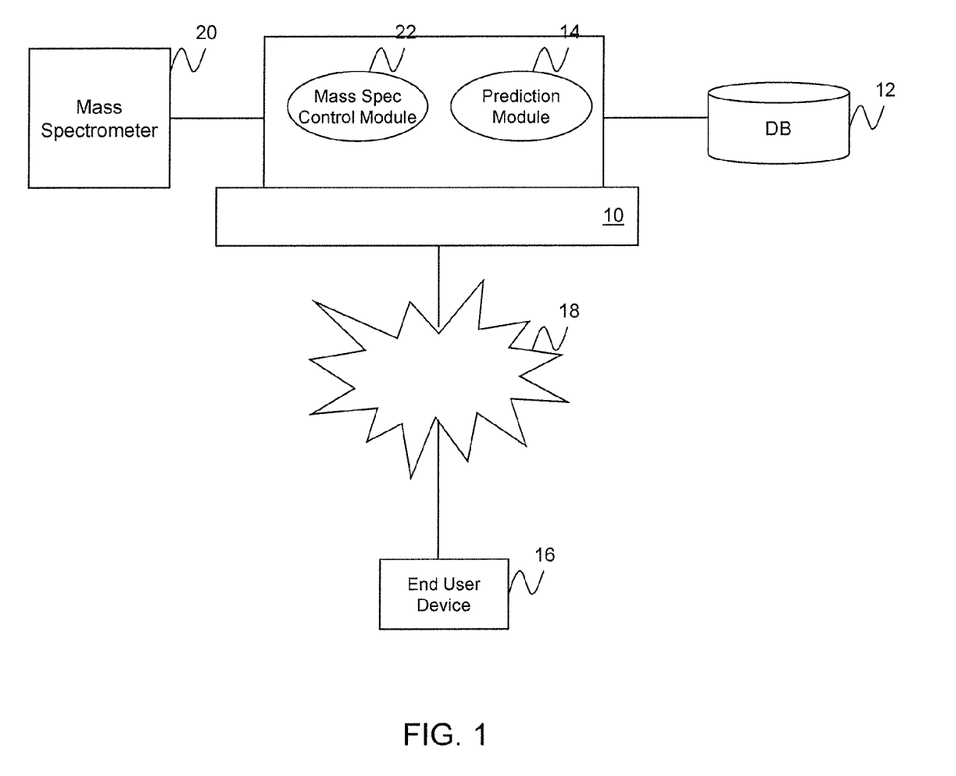
FIG. 1 is a block diagram of a prediction system including a computer device configured to predict the isotopic anatomy of different molecules according to one embodiment of the invention.

FIG. 1 is a block diagram of a prediction system including a computer device 10 configured to predict the isotopic anatomy of different molecules according to one embodiment of the invention. The computer device 10 may be a server, standalone computer, laptop, or any other data processing device conventional in the art.

The computer device 10 is coupled to a mass spectrometer 20 such as the high-resolution mass spectrometer described in U.S. application Ser. No. 13/656,447, which is incorporated herein by reference. According to one embodiment, the mass spectrometer receives a molecule sample and produces a mass spectrum for the sample which may then be analyzed to determine the isotopic composition of the sample.

According to one embodiment, the computer device 10 includes a central processing unit (CPU) which executes software instructions and interacts with other system components to provide the various functionalities of the prediction system. For example, the software instructions may be for controlling the mass spectrometer 20, predicting the isotopic anatomy of an input molecule, refining the prediction based on actual observations, and making conclusions based on the predicted isotopic anatomy. An input device, such as a mouse-type controller or keyboard, facilitates user control of the operation of the computer device 10. A display screen coupled to the computer device 10 may display results of the analysis of the input molecule.

The computer device 10 is also coupled to a storage device 12 such as, for example, a disk drive or drive array for long-term storage of data used by the prediction system. For example, the storage device 12 may host a database of records of different molecules where each record provides a list of isotopic species for the molecule and their relative positions in a mass spectrum (e.g. by listing the mass to charge ratio (AMU) of each species). Each record may also include other information such as, for example, the commonly observed proportions of fragment and adduct ions generated in the ion source of the mass spectrometer 20, the relationships between isotope abundances in the molecule of interest and isotope abundances in those fragment ions, and commonly observed rates of other ion source processes, such as exchange of isotopes between ion species, and recombination of ion fragments. According to one embodiment, the record incorporates information obtained prior to the measurement through independent study of standard materials, such as the common or average abundances of isotopes in natural materials, and experimentally observed fragmentation spectra under common analytical conditions in mass spectrometers of similar design to that used in this system.

The computer device 10 further includes an addressable memory for storing the software instructions for execution by the CPU. The memory is implemented using a standard memory device, such as, for example, a random access memory (RAM). In one embodiment, the memory stores a number of software objects or modules, including a prediction module 14 and a mass spectrometer control module 22. The mass spectrometer control module 22 includes computer program instructions for controlling different aspects of the mass spectrometer 20, such as, for example, the position and sensitivity of detectors of a detector array.

The prediction module 14 includes computer program instructions for predicting the isotopic anatomy of an input molecule. Although the various modules are assumed to be separate functional units, a person of skill in the art will understand that the functionality of various modules may be combined or integrated into a single module, or subdivided into further sub-modules as will be apparent to the person of skill in the art. The mass spectrometer control module 22 and the prediction module 14 may also be hosted in separate processing units. For example, the mass spectrometer control module 22 may be hosted by a processing unit in the mass spectrometer 10 while the prediction module 14 may be hosted by a processing unit in the computer device 10.

If the computer device 10 is a server, one or more end user devices 16 may access the mass spectrometer control module 22 and/or prediction module 14 over a data communications network 18. The data communications network may be a local area network, a private wide area network, or a public wide area network such as the Internet.

Figure 2:
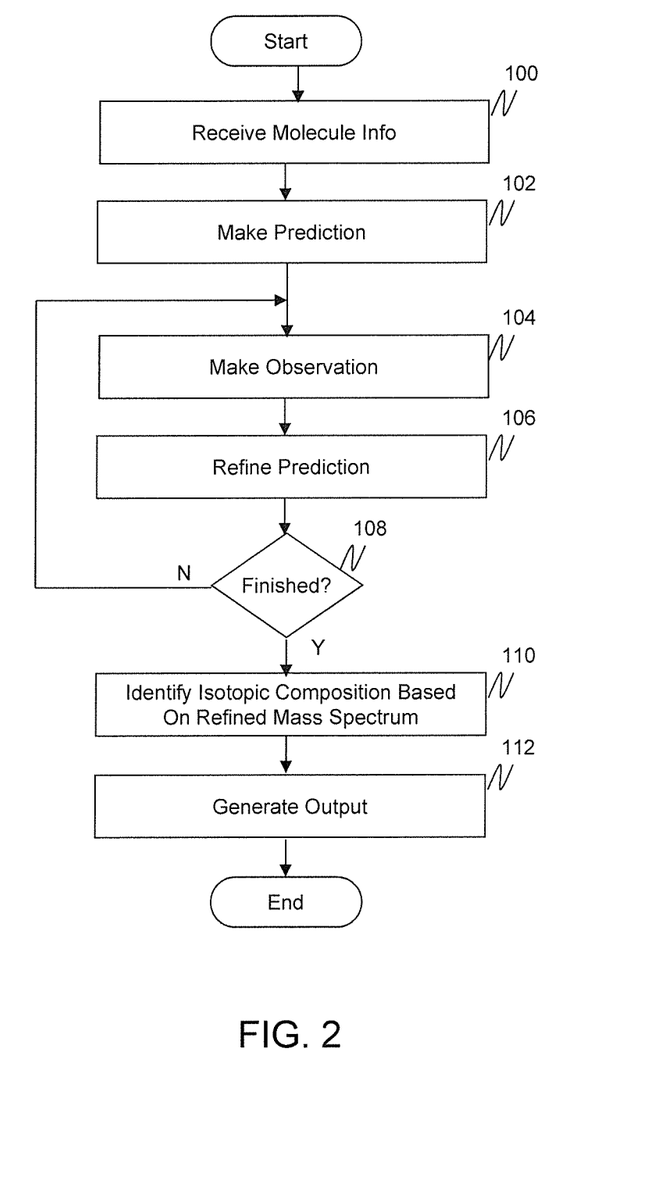
FIG. 2 is a flow diagram of a process executed by a prediction module for predicting the isotopic anatomy of a molecule according to one embodiment of the invention.

FIG. 2 is a flow diagram of a process executed by the prediction module 14 for predicting the isotopic anatomy of a molecule according to one embodiment of the invention. The problem that is to be solved by the prediction module may be defined as follows: given a composition space having various axes where each axis defines the abundance of a specific isotopic species (also referred to as an isotopologue of the molecule), locate the molecule within the composition space with a threshold (or at least specified) degree of certainty. The process of FIG. 2 may be described in terms of a software routine executed by the CPU of the computer device 10 based on instructions stored in the memory of the computer device. The instructions may also be stored in other non-transient computer readable media such as, for example, a CD-ROM, flash drive, or the like. A person of skill in the art should recognize that the routine may be also executed via hardware, firmware (e.g. via an ASIC), or in any combination of software, firmware, and/or hardware. Furthermore, the sequence of steps of the process is not fixed, but can be altered into any desired sequence as recognized by a person of skill in the art.

The process starts, and in step 100, the prediction module 14 receives information on a molecule to be analyzed. In this regard, the prediction module 14 provides a graphical user interface to prompt a user to provide identification information of the molecule that is to be analyzed. For example, the user may identify the molecule to be analyzed as $H_2$ (i.e., molecular hydrogen). The graphic user interface may, throughout the process, ask for other inputs and decisions from the user. According to one embodiment, the user may be prompted to specify assumed or estimated initial values for the D/H ratio of the same, the proportion of its D present as D2, the probabilities for formation of $H^+$ fragment ions or $H_3^+$ adduct ions, and the mass resolution of the mass spectrometer. The user may utilize keyboard, keypad, or other input device for providing the requested information. According to some embodiments, some or all of these parameters might be read from stored data generated on a previous sample or standard, or assumed based on common values for analyses of natural materials at typical instrument conditions.

In step 102, the prediction module 14 makes an initial guess or prediction of the mass spectrum for the identified molecule. According to one embodiment, the initial prediction of the mass spectrum is based on an initial guess or user-input value for the mass resolution of the mass spectrometer, common abundances of the relevant isotopes in natural samples of the molecule of interest, the probabilities of forming certain fragments, adducts and other ion species generated in the ion source, and the assumed proportions of isotopes in various positions.

In this regard, the prediction module retrieves from the storage device a record stored for the identified molecule. According to one embodiment, the retrieved record contains the isotopic composition of a standard which may be, for example, a sample of the molecule of interest which has a known or assumed composition; other samples are compared with this standard, such that relative differences between measured isotope abundances in unknown sample and standard sample can serve as the basis for reporting the composition of the unknown sample. The record of the molecule might include the possible isotopes and isotopologues (versions of the molecule that differ in their isotopic content) for the standard, the fragmentation spectrum (fragments and adducts) for the standard, and typical interferences that are commonly present for the standard. For example, the record for the molecule $H_2$ may indicate the existence of the following species and their proportional abundance in a standard:

Isotopic species: hydrogen (H), deuterium (D), and tritium (T)

Isotopologues: $H_2$, HD, HT, $D_2$, DT, and $T_2$

Fragment ions: $H^+$, $D^+$, $T^+$

Molecular ions: $H_2^+$, $HD^+$, $HT^+$, $D_2^+$, $DT^+$, and $T_2^+$

Adduct ions: $H_3^+$, $H_2D^+$, $D_2H^+$, $D_3^+$, $HDT^+$, $D_2T^+$, $T_2H^+$, $T_2D^+$, $T_3^+$ Possible interfering ions: $^3He^+$, $^4He^+$, $^{12}C^{+4}$, $^{12}C^{+3}$, etc.

According to one embodiment, the record includes a matrix of algebraic operators that relate certain of these quantities to one another. For example, one particular algebraic operator may relate abundance ratios of isotopic species in the sample (HD, D2) to related ion species that are detected by the mass spectrometer (HD+/H2+) through a constant of proportionality, aHD/H2: HD+/H2+=aHD/H2× (HD/H2). A large set of such values exist, which are generically referred to as ai values. Another algebraic operator might define the probability of formation of a fragment ion to be a function of abundances of molecules capable of making that fragment, the intensity of some reference molecular ion, and some constant of proportionality. For example:

$$H^+/H_2^+ = K_{fragment} \times [(2 \times H_2 + HD + HT)/H_2]$$

One or more algebraic operators might also define variations that describe relationships between proportions of isotopologues in a sample, such as expressions derived from the mass action constants for isotope exchange reactions; e.g.:

$$K_{eq}^1 = (H2 \times D2)/(HD)2$$

I.e., $K_{eq}^1$ has a value equal to the mass action expression for the reaction: $2HD = H_2 + D_2$ According to one embodiment, the user is prompted by the GUI to select the species that he or she would like considered in predicting the composition of the identified molecule. For example, after being presented with a list of isotopes that can exist for the molecule, the user may indicate that only a subset of the isotopes are to be considered (e.g. consider H and D but ignore T). Furthermore, the user may indicate that only a subset of the isotopolgues are to be considered (e.g. consider only $H_2$ and HD but not $D_2$). The user may also be asked by the GUI whether the typical interferences for the molecule are to be considered (e.g., the interference of $^3$He with HD), and further prompted to make other decisions such as, for example, decisions relating to the tuning of the mass spectrometer (e.g. request the user to enter a resolution for the mass spectrometer).

In step 104, the user makes an express observation of the mass spectrum of one or more species of the molecule. In this regard, the user invokes the mass spectrometer 20 and provides to the mass spectrometer the one or more species for observation. The mass spectrometer produces an observed mass spectrum for the one or more species according to the method described in the above-referenced U.S. application Ser. No. 13/656,447.

In step 106, the initial prediction of the mass spectrum of the module is refined based on the observed mass spectrum of one or more species of the molecule. According to one embodiment, this refinement may involve adjustment of assumed quantities in the record for that molecule (e.g., the values of $\alpha_i$ or $K_{fragment}$ in the examples above) to minimize the degree of disagreement between the observed mass spectrum and the mass spectrum implied by the quantities assumed in the record. According to one embodiment, the adjustment of assumed quantities may be done automatically by the prediction module 14, or in response to a user command. Generally speaking, a user will perform this fitting exercise first for a measurement of a standard, for which the abundances of isotopic species (e.g., $H_2$, $D_2$, HD, HT, $K_{eq}^1$, etc. in the example above) are nominally known but the quantities that relate measured known isotopologue abundances to measured ion intensities (e.g., quantities such as $\alpha_i$ and $K_{fragment}$ in the example above) are not known. Generally, samples and standards are analyzed sequentially under similar measurement conditions, such that the measurement of a standard can be used to solve for quantities that relate isotope abundances to ion abundances (e.g., $\alpha_i$ and $K_{fragment}$ values), and the resulting fitted values of those quantities can then be used to relate measured ion abundances in an unknown sample to that sample's abundances of isotopic species (e.g., in this instance, one knows $\alpha_i$ and $K_{fragment}$ based on a measurement of the standard, and the statistical fit of the measured spectrum to the modeled spectrum assumes these values and solves for the unknown abundances of isotopic species, $H_2$, HD, $D_2$, etc.). According to one embodiment, this minimization follows principles of Bayesian statistics for instances in which only a subset of ion species are observed in the measurement.

The user is presented with a statement of revised properties of the sample (e.g., estimated abundances of isotopic species derived by calculating the best fit to the measured mass spectrum of the sample, including derived properties such as $K_{eg}^1$). The user is also presented with a measure of the goodness of fit between the measured mass spectrum and the adjusted model (e.g., an error in a least squares sense, or some other statistical measure of goodness of fit as is conventional in the art). The user is further presented, in step 108, via prompts via the GUI, with the opportunity to either stop the analysis, accept the revised model of the sample properties, or refine the analysis of that sample through additional observations. If the user transmits a command to refine the analysis, the process returns to step 104 to make further observations, and the prediction is further refined to be consistent with the current observation as well as all past observations. In this manner, the predicted mass spectrum for the molecule is iteratively refined based on express observations of mass spectrums of specific species.

If the refined prediction of the mass spectrum is acceptable, the prediction module 14 identifies the isotopic composition of the molecule in step 110, based on the refined mass spectrum. As a person of skill in the art will appreciate, the more refined the mass spectrum, the more accurate the identified isotopic composition based on the refined mass spectrum. In identifying the isotopic composition of the analyzed molecule, the prediction module 14 identifies all species with masses for which an intensity is depicted in the mass spectrum, or which can be inferred based on the measured intensity of one or more ionic species, through the matrix of algebraic operators that define relationships among isotopic and ionic species.

In step 112, the prediction module 14 generates an output based on the identified isotopic composition. For example, the output may identify differences between the composition of the input molecule and the composition of a standard. The output may also identify differences between the composition of the input molecule and some reference state of isotopic ordering in an idealized version of the molecule. For example, the output might identify the difference in composition between the analyzed molecule and a version of the molecule in which the probability of isotopic substitution in each atomic site is random, or stochastic. The identified isotopic composition may also be associated with other properties of the sample such as, for example, a temperature at which the identified composition would represent thermodynamic equilibrium. For example, a derived quantity such as $K_{eg}^1$ may have some known relationship to temperature. In this case, the prediction module 14 includes this temperature in the output.

Figure 3:
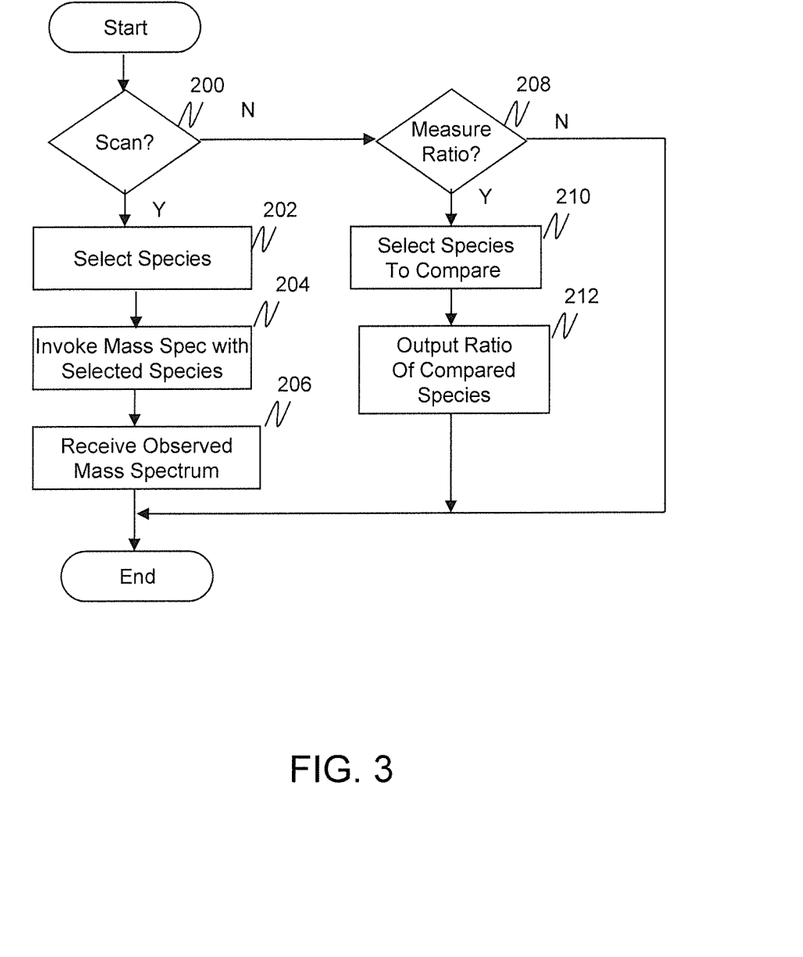
FIG. 3 is a more detailed flow diagram of a step of making an observation according to one embodiment of the invention.

FIG. 3 is a more detailed flow diagram of step 104 of FIG. 2 of making an observation according to one embodiment of the invention. In step 200, the prediction module 14 determines based on data entered by the user, whether the observation to be performed is a scan. If the answer is YES, the prediction module prompts the user to select the species or mass range to be scanned in step 202. In step 204, the prediction module invokes the mass spectrometer control module 22 for conducting the scan of the selected species. The user also provides the actual samples corresponding to the selected species to the mass spectrometer 20 as described in further detail in U.S. Provisional Application No. 61/550,272. The prediction module then receives the mass spectrum produced by the mass spectrometer in step 206.

Referring again to step 200, if the observation is not to perform a scan, a determination is made in step 208 as to whether the observation is to measure a ratio. If the answer is YES, the prediction module prompts the user to select the species for which a ratio is to be computed in step 210. The prediction module compares the intensities of the selected species and outputs the computed ratio in step 212. In measuring the ratio, the mass spectrometer 20 may be invoked to measure the intensity at the molecular mass corresponding to the first selected species while concurrently measuring the intensity at another molecular mass corresponding to the second selected species.

Figure 4:
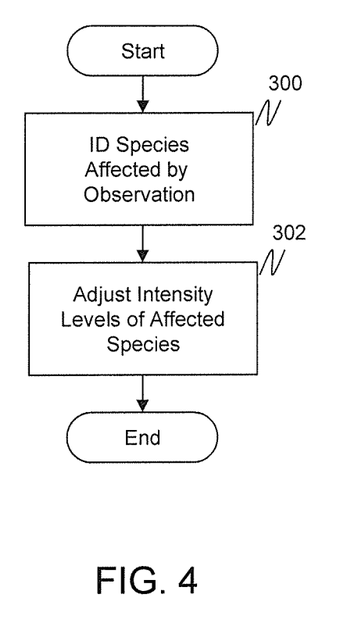
FIG. 4 is a more detailed flow diagram of a step of refining the predicted mass spectrogram according to one embodiment of the invention.

FIG. 4 is a more detailed flow diagram of step 106 of FIG. 2 of refining the predicted mass spectrogram according to one embodiment of the invention.

In step 300, the prediction module identifies the species affected by the observation. For example, the species expressly selected by the user for observation are directly affected by the observation (e.g. via a direct measurement of the intensity of the selected species) and thus selected. Other species, although not directly observed, may still be affected due to the observation. For example, the measurement of a ratio of the intensity of two specific species may influence the estimated abundances or abundance ratios of other species. In the example of molecular hydrogen, above, a measurement of the $HD^+/H_2^+$ ion intensity ratio, combined with independently known values of $\alpha_{HD/H2}$ and a relevant value of $K_{fragment}$ (for example, based on concurrent measurement of a standard of known isotopic composition) will imply an expected value of $D^+/H^+$ in the sample, even if that ratio is not measured in the sample. As noted above with reference to the example application to $H_2$, according to one embodiment, the record for the analyzed molecule specifies the relationship between the species via, for example, one or more equations (e.g., those defining ai, Kfragment and Keq1). Other exemplary equations include, but are not limited to equations that compute an adduct probability and compute a redistribution probability. Thus, in step 300, all species that are constrained by a current observation are identified and selected for adjustment.

In step 302, the prediction module adjusts the intensity levels of the directly and indirectly affected species to be consistent with the current observations (as well as all past observations). For example, if the output of the observation is a scan of specifically identified species, the intensity of those species are adjusted in the predicted mass spectrogram to be consistent with the observed intensities. If the output of the observation is a measured ratio, the relative intensities of all affected species are adjusted to be consistent with the measured ratio. For example, assume that the molecule to be analyzed is methane. The user selects to observe parts of the mass 16 and 17 AMU mass peaks and determine the ratio: $^{13}CH_4^+/^{12}CH_4^+$. Based on this measured ratio, the prediction module automatically calculates the predicted relative abundances of the $CH_3^+$ fragment ions: $^{13}CH_3^+/^{12}CH_3^+$, because both the numerator and denominator share the same fragmentation probability constant (e.g., chances of making a $CH_3^+$ instead of a $CH_4^+$; this constant serves a role similar to that of $K_{fragment}$ in the example of $H_2$ explained above). In this manner, the prediction module automatically predicts the relative intensities of the $^{13}CH_3^+$ species at mass 16 AMU and the $^{12}CH_3^+$ species at mass 15 AMU, without input of specific observation data for these species.

According to one embodiment of the invention, after adjusting the prediction and before making another observation, the prediction module recommends a list of species that should be observed next. According to one embodiment, the species are ranked in an order of importance. The importance may be determined based on, for example, how much the error in the overall fit between model and observed spectrum would shrink if each species in the list is observed. In other words, the importance may be determined based on how the volume of the composition space for the analyzed molecule will shrink based on the observation. According to one embodiment, the module provides a ranked list of species, measurement of which would best constrain a derived property such as $K_{eg}^1$. According to one embodiment, the module includes sub-routines which predict the error with which each potentially analyzable ion species could be measured, based on prior measurements of that sample (considering, for example, intensities of previously analyzed beams, the mass resolution of the instrument in its current configuration, and other variables). According to one embodiment, the sub-routine may implement well known algorithms, such as, for example, a least squares error algorithm or other conventional statistical data fitting algorithms conventional in the art for predicting the error. The prediction module is thus configured to take a species that has not yet been observed, assume that it was observed within a certain error, recompute the composition based on the hypothetical observation, and calculate how much the error shrinks based on the recomputed composition. For example, the adducts for a particular molecule may be small and thus, any express observation would not measure it to a certain precision. Thus, it would not be useful to expressly observe the adducts. The adducts would thus be listed at the bottom of a ranked list, or not listed at all.

Figure 5:
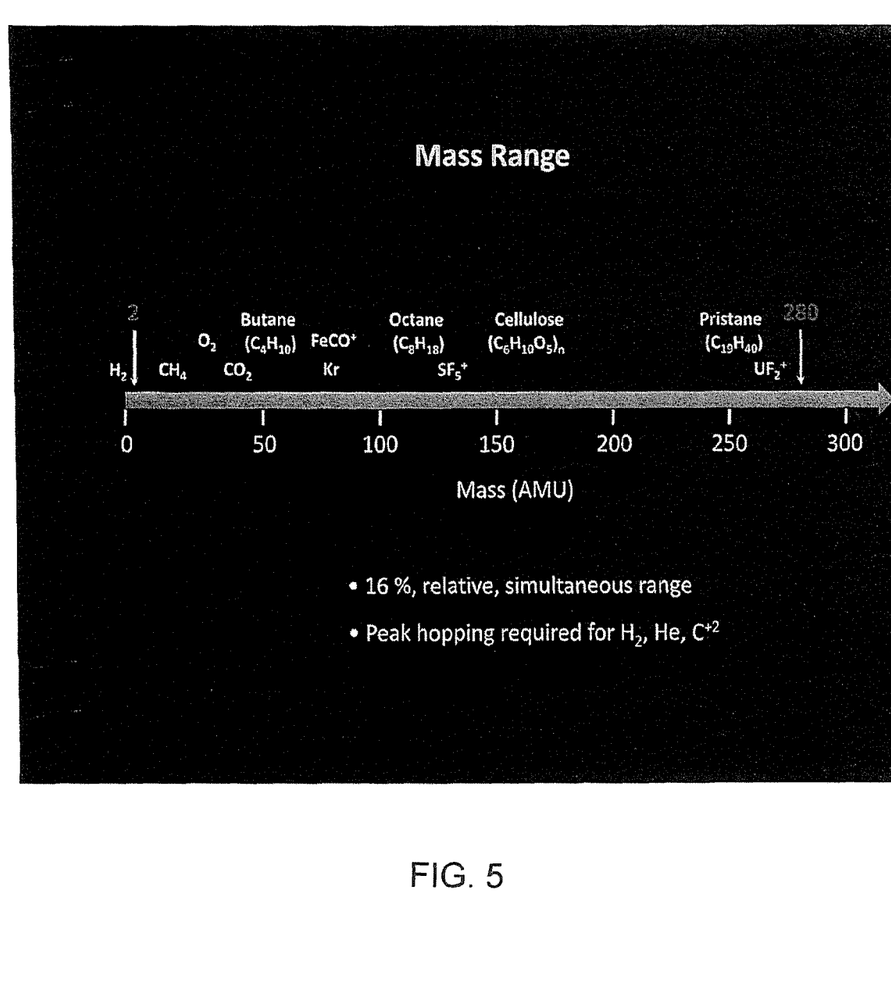
FIG. 5 is an exemplary schematic diagram of a mass range for different types of molecules.
Figure 6:
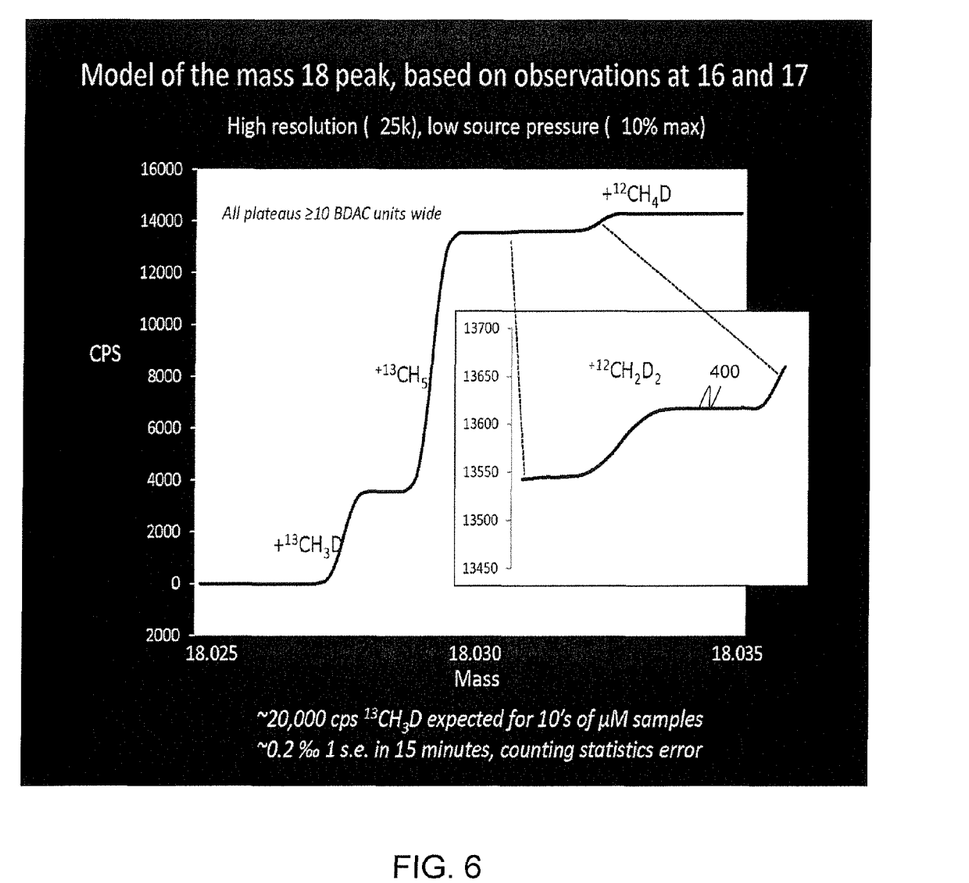
FIG. 6 is an exemplary schematic diagram of a portion of a mass spectrogram associated with mass 18.

FIG. 5 is an exemplary schematic diagram of a mass range for different types of molecules, and FIG. 6 is an exemplary schematic diagram of a portion of a mass spectrogram associated with mass 18. The mass spectrogram creates ziggurat-shaped peaks when a family of species of a particular cardinal mass are scanned across a detector. In this example, a specific observation of the molecule $^{+2}CH_2D_2^+$ causes the adjustment of the intensity level of the mass spectrogram between 18.030 AMU and 18.035 AMU as shown by line 400.

Figure 7:
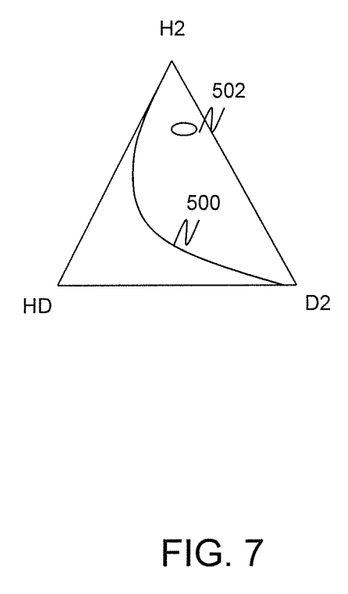
FIG. 7 is a schematic diagram of an exemplary composition space for $H_2$.

FIG. 7 is a schematic diagram of an exemplary composition space for $H_2$. The prediction module 14 identifies a location 502 in the composition space for a molecule to be analyzed. Given this location, one may determine, for example, how far the predicted composition is from a stochastic distribution 500.

According to one embodiment, the predicted composition of a molecule may be used for various applications including applications in gas thermometry, forensic tracking, biomedical research, and the like, as further described in the above-referenced U.S. application Ser. No. 13/656,447. For example, the predicted composition of a sample taken from a natural gas field may indicate whether the field is appropriate for natural gas exploration based on the temperature of equilibrium consistent with the measured composition of an analyzed sample of methane molecules. According to this example, the prediction module 14 may be configured to identify the relative abundance of specific isotopologues, and from this information, make a temperature calculation (in a way analogous to the example of the $K_{eq}^1$ value for $H_2$, given above). Such temperate calculation may be based on a knowledge of the equilibrium constant of a reaction of certain isotopologues of methane, and the temperature associated with such equilibrium constant. The calculated temperature may be used to output a recommendation to a user as to whether there is a likelihood of finding natural gas in the location from which the sample was taken. The recommendation may be displayed on a computer screen, printed, or stored in memory.

Although this invention has been described in certain specific embodiments, those skilled in the art will have no difficulty devising variations to the described embodiment which in no way depart from the scope and spirit of the present invention. Furthermore, to those skilled in the various arts, the invention itself herein will suggest solutions to other tasks and adaptations for other applications. It is the applicants intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive, the scope of the invention to be indicated by the appended claims and their equivalents rather than the foregoing description.

The invention claimed is:

1. A non-transitory computer readable medium containing computer instructions stored therein for causing a computer processor to predict an isotopic anatomy of a molecule by:
   receiving information of a molecule having a plurality of isotopic species;
   generating a prediction of the isotopic anatomy of the molecule, wherein the generating the prediction includes retrieving, from a record stored in a database, isotopic composition of a real sample having a known or assumed composition;
   identifying one or more isotopic species output in response to the prediction;
   controlling at least one aspect of a mass spectrometer for making an observation of the identified isotopic species, wherein the observation includes computing a ratio of abundance of a first one of the identified isotopic species against abundance of a second one of the identified isotopic species;
   automatically refining the prediction of the isotopic anatomy of the molecule based on the observation; and
   generating an output indicative of the isotopic anatomy of the molecule.

2. The non-transitory computer readable medium of claim 1, wherein the isotopic anatomy of the molecule is a mass spectrum of the molecule.

3. The non-transitory computer readable medium of claim 1, wherein the isotopic anatomy of the molecule is the isotopic composition of the molecule.

4. The non-transitory computer readable medium of claim 1, wherein the prediction of the isotopic anatomy considers presence of interferences.

5. The non-transitory computer readable medium of claim 1, wherein the prediction of isotopic anatomy considers a fragmentation spectrum.

6. The non-transitory computer readable medium of claim 1, wherein the prediction is based on the isotopic anatomy of the sample having a known or assumed composition.

7. The non-transitory computer readable medium of claim 1, wherein generating the prediction includes estimating abundance of one or more of the plurality of isotopic species via one or more algebraic operators that define relationships among the isotopic species.

8. The non-transitory computer readable medium of claim 1, wherein the generating the prediction includes generating a predicted mass spectrum for the molecule.

9. The non-transitory computer readable medium of claim 1, wherein the refining the prediction includes refining the abundance of the two other isotopic species relative to each other, wherein the abundance is not expressly measured.

10. The non-transitory computer readable medium of claim 1, wherein the program instructions further comprise:
   recommending one or more of the plurality of isotopic species for observation.

11. The non-transitory computer readable medium of claim 1, wherein the program instructions further comprise:
identifying a property of the molecule based on the predicted isotopic anatomy of the molecule; and
outputting a recommendation based on the identified property.

12. The non-transitory computer readable medium of claim 8, wherein the making the observation includes performing a mass scan of one or more of the isotopic species and outputting a measured mass spectrum of the one or more isotopic species.

13. The non-transitory computer readable medium of claim 10, wherein the recommendation is based on estimated shrinking of a composition space based on observation of the recommended one or more of the plurality of isotopic species.

14. The non-transitory computer readable medium of claim 11, wherein the identified property is temperature.

15. The non-transitory computer readable medium of claim 12, wherein the refining the prediction includes calculating a fitness value between the measured mass spectrum and the predicted mass spectrum.

16. The non-transitory computer readable medium of claim 12, wherein the refining the prediction includes identifying one or more of the plurality of isotopic species affected by the observation.

17. The non-transitory computer readable medium of claim 16, wherein the species affected by the observation include species not expressly observed by performing the mass scan.

18. The non-transitory computer readable medium of claim 17, wherein the refining includes estimating abundances of the species not expressly observed, based on one or more algebraic equations that define relationships of the species not expressly observed, with species that are observed.

19. A non-transitory computer readable medium containing computer instructions stored therein for causing a computer processor to predict an isotopic anatomy of a molecule by:
receiving information of a molecule having a plurality of isotopic species;
generating a prediction of the isotopic anatomy of the molecule, wherein the generating the prediction includes retrieving, from a record stored in a database, isotopic composition of a real sample having a known or assumed composition;
identifying one or more isotopic species output in response to the prediction;
controlling at least one aspect of a mass spectrometer for making an observation of the identified isotopic species, wherein the observation includes computing a ratio of abundance of a first one of the identified isotopic species against abundance of a second one of the identified isotopic species;
automatically refining the prediction of the isotopic anatomy of the molecule based on the observation;
generating an output indicative of the isotopic anatomy of the molecule; and
outputting a recommendation based on the isotopic anatomy of the molecule, wherein the recommendation relates to likelihood of finding natural gas at a place where a sample of the molecule was obtained.

20. A system for predicting an isotopic anatomy of a molecule, the system comprising:
a mass spectrometer;
a mass storage device hosting a database;
a processor coupled to the mass storage device; and
a memory, wherein the memory includes instructions that, when executed by the processor, cause the processor to:
receive information of a molecule having a plurality of isotopic species;
generate a prediction of the isotopic anatomy of the molecule, wherein the generating the prediction includes retrieving, from a record stored in the database, isotopic composition of a real sample having a known or assumed composition;
identify one or more isotopic species output in response to the prediction;
control at least one aspect of the mass spectrometer for making an observation of the identified isotopic species, wherein the observation includes computing a ratio of abundance of a first one of the identified isotopic species against abundance of a second one of the identified isotopic species;
automatically refine the prediction of the isotopic anatomy of the molecule based on the observation; and
generate an output indicative of the isotopic anatomy of the molecule.

21. The system of claim 20, wherein the isotopic anatomy of the molecule is a mass spectrum of the molecule.

22. The system of claim 20, wherein the isotopic anatomy of the molecule is the isotopic composition of the molecule.

23. The system of claim 20, wherein the instructions that cause the processor to predict the isotopic anatomy include instructions that cause the processor to consider presence of interferences.

24. The system of claim 20, wherein the prediction of isotopic anatomy considers a fragmentation spectrum.

25. The system of claim 20, wherein the prediction is based on the isotopic anatomy of the sample having a known or assumed composition.

26. The system of claim 20, wherein the instructions that cause the processor to generate the prediction include instructions that cause the processor to estimate abundance of one or more of the plurality of isotopic species via one or more algebraic operators that define relationships among the isotopic species.

27. The system of claim 20, wherein the instructions that cause the processor to generate the prediction include instructions that cause the processor to generate a predicted mass spectrum for the molecule.

28. The system of claim 20, wherein the instructions that cause the processor to refine the prediction include instructions that cause the processor to refine the abundance of the two other isotopic species relative to each other, wherein the abundance is not expressly measured.

29. The system of claim 20, wherein the instructions further cause the processor to:
recommend one or more of the plurality of isotopic species for observation.

30. The system of claim 20, wherein the instructions further cause the processor to:
identify a property of the molecule based on the predicted isotopic anatomy of the molecule; and
output a recommendation based on the identified property.

31. The system of claim 27, wherein the instructions that cause the processor to make the observation include instructions that cause the processor to perform a mass scan of one or more of the isotopic species and output a measured mass spectrum of the one or more isotopic species.

32. The system of claim 29, wherein the recommendation is based on estimated shrinking of a composition space based on observation of the recommended one or more of the plurality of isotopic species.

33. The system of claim 30, wherein the identified property is temperature.

34. The system of claim 31, wherein the instructions that cause the processor to automatically refine the prediction include instructions that cause the processor to calculate a fitness value between the measured mass spectrum and the predicted mass spectrum.

35. The system of claim 31, wherein the instructions that cause the processor to refine the prediction include instructions that cause the processor to identify one or more of the plurality of isotopic species affected by the observation.

36. The system of claim 35, wherein the species affected by the observation include species not expressly observed by performing the mass scan.

37. The system of claim 36, wherein the instructions that cause the processor to refine the predicting include instructions that cause the processor to estimate abundances of the species not expressly observed, based on one or more algebraic equations that define relationships of the species not expressly observed, with species that are observed.

38. A system for predicting an isotopic anatomy of a molecule, the system comprising:
   a mass spectrometer;
   a mass storage device hosting a database;
   a processor coupled to the mass storage device; and
   a memory, wherein the memory includes instructions that, when executed by the processor, cause the processor to:
   receive information of a molecule having a plurality of isotopic species;
   generate a prediction of the isotopic anatomy of the molecule, wherein the generating the prediction includes retrieving, from a record stored in the database, isotopic composition of a real sample having a known or assumed composition;
   identify one or more isotopic species output in response to the prediction;
   control at least one aspect of the mass spectrometer for making an observation of the identified isotopic species, wherein the observation includes computing a ratio of abundance of a first one of the identified isotopic species against abundance of a second one of the identified isotopic species;
   automatically refine the prediction of the isotopic anatomy of the molecule based on the observation;
   generate an output indicative of the isotopic anatomy of the molecule;
   output a recommendation based on the isotopic anatomy of the molecule, wherein the recommendation relates to likelihood of finding natural gas at a place where a sample of the molecule was obtained.

* * * * *

UNITED STATES PATENT AND TRADEMARK OFFICE
CERTIFICATE OF CORRECTION

PATENT NO.        : 9,594,879 B2
APPLICATION NO.   : 13/656577
DATED             : March 14, 2017
INVENTOR(S)       : John M. Eiler Page 1 of 1

It is certified that error appears in the above-identified patent and that said Letters Patent is hereby corrected as shown below:

In the Specification

Column 5, Line 4, should read

According to one embodiment, the user may be prompted to specify assumed or estimated initial values for the D/H ratio of the same, the proportion of its D present as $D_2$, the probabilities for formation of $H^+$ fragment ions or $H_3^+$ adduct ions, and the mass resolution of the mass spectrometer.

Column 5, Line 52, should read

According to one embodiment, the record includes a matrix of algebraic operators that relate certain of these quantities to one another. For example, one particular algebraic operator may relate abundance ratios of isotopic species in the sample (HD, $D_2$) to related ion species that are detected by the mass spectrometer ($HD^+/H_2^+$) through a constant of proportionality, $\alpha HD/H_2$: $HD^+/H_2^+ = \alpha HD/H_2 \times (HD/H_2)$. A large set of such values exist, which are generically referred to as $\alpha_i$ values.

Column 6, Line 1, should read

One or more algebraic operators might also define variations that describe relationships between proportions of isotopologues in a sample, such as expressions derived from the mass action constants for isotope exchange reactions; e.g.:
$K_{eq}^1 = (H_2 \times D_2)/(HD)_2$ Signed and Sealed this
Seventeenth Day of April, 2018

Andrei Iancu
*Director of the United States Patent and Trademark Office*